(12) United States Patent
Carlo et al.

(10) Patent No.: US 7,048,948 B2
(45) Date of Patent: May 23, 2006

(54) STABLE GRANULATES CONTAINING S-ADENOSYLMETHIONINE AND PROCESS FOR THE PREPARATION THEREOF

(76) Inventors: Cantabene Carlo, Via Breganzona 6, CH 6900 Lugano Besso (CH); Magri' Paolo, Via Francesco Anzani 52, 22100 Como (IT); Michele Muller, Via Vignora, 6927 Agra (CH)

( * ) Notice: Subject to any disclaimer, the term of this patent is extended or adjusted under 35 U.S.C. 154(b) by 0 days.

(21) Appl. No.: 10/432,338

(22) PCT Filed: Nov. 29, 2002

(86) PCT No.: PCT/EP02/13568

§ 371 (c)(1),
(2), (4) Date: May 20, 2003

(87) PCT Pub. No.: WO03/053412

PCT Pub. Date: Jul. 3, 2003

(65) Prior Publication Data

US 2004/0106573 A1   Jun. 3, 2004

(30) Foreign Application Priority Data

Dec. 12, 2001   (EP) ................................. 01204863

(51) Int. Cl.
*A61K 9/14*   (2006.01)
*A61K 9/16*   (2006.01)
(52) U.S. Cl. .................... 424/489; 424/490; 424/494
(58) Field of Classification Search ................ 424/489, 424/490, 494, 499; 514/952, 954
See application file for complete search history.

(56) References Cited

U.S. PATENT DOCUMENTS

| | | | | |
|---|---|---|---|---|
| 5,254,347 A | * | 10/1993 | Samejima et al. | .......... 424/495 |
| 5,466,678 A | * | 11/1995 | Kawabata et al. | ............ 514/46 |
| 2004/0091529 A1 | * | 5/2004 | Edgren et al. | ............... 424/468 |

FOREIGN PATENT DOCUMENTS

| | | |
|---|---|---|
| EP | 0136464 A2 | 4/1985 |
| EP | 0162324 A1 | 11/1985 |
| EP | 019133 A2 | 8/1986 |
| EP | 0387757 A2 | 9/1990 |
| EP | 0827964 A2 | 3/1998 |
| WO | WO99/62524 | 12/1999 |

OTHER PUBLICATIONS

Rambali et al. "Using experimental design to optimize the process parameters in fluidized bed granulation on a semi-full scale," Int. J. Pharmaceutics (Jun. 4, 2001) 220 (1-2): 149-60.*
Webster's II New Riverside University Dictionary (1994) (Houghton-Mifflin: Boston, MA) p. 120.*

* cited by examiner

*Primary Examiner*—Jean C. Witz
*Assistant Examiner*—Susan Hanley
(74) *Attorney, Agent, or Firm*—Stephen M. Nipper; Dykas, Shaver & Nipper

(57) ABSTRACT

A fluid bed granulation process for manufacturing non-hygroscopic, stable granulates containing a water-soluble salt of S-adenosylmethionine is described. Said process comprises:
  a) the simultaneous, sequential or alternate dispersion of at least a solution of a water-soluble salt of SAMe (A) and of a solution of a coating agent (B), on a fluid bed granulation carrier (C) and
  b) the fluid bed granulation of the mixture.

Granulates obtainable by said process and solid oral pharmaceutical forms obtainable by said granulates are disclosed.

23 Claims, No Drawings

STABLE GRANULATES CONTAINING S-ADENOSYLMETHIONINE AND PROCESS FOR THE PREPARATION THEREOF

The present invention relates to a granulation process and, more particularly, it relates to a granulation process for preparing stable granulates containing S-adenosylmethionine.

S-adenosylmethionine, in short SAMe, is a known compound of formula

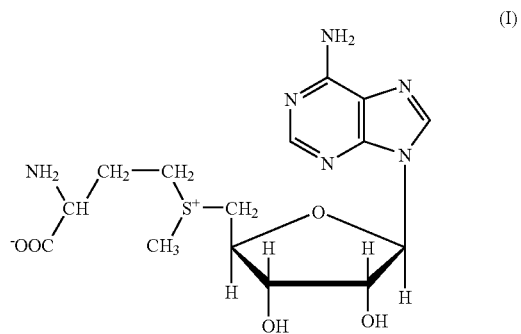

broadly used in therapy, especially for its anti-inflammatory properties and in the treatment of chronic hepatic diseases (Merck Index, 1996, n. 155).

It is generally prepared by fermentation and isolated as a salt, as described for example in the U.S. Pat. No. 4,562,149.

The molecule is characterized by a significant intrinsic instability, mainly due to the intramolecular attack of the carboxylate ion onto the methylene in beta position, providing homoserine and methylthioadenosine.

This high instability, that appears both in the solid state and as an aqueous solution at room temperature already, makes the isolation, the storage and the formulation of the product particularly difficult.

In order to obviate to these problems of decomposition, many studies have been undertaken and several solutions proposed.

First of all it was discovered that the salts of SAMe with bulky anions are significantly more stable. Therefore many salts of SAMe, more stable, both water-soluble, such as sulfates, tosylates (U.S. Pat. No. 4,562,149) or polymeric polycarboxylates (EP191133), and liposoluble, such as for example the long chain sulfosuccinates described in EP162324 have been prepared.

Nevertheless the water-soluble salts of SAMe currently on the market, such as for example the disulfate tosylate or the 1,4-butandisulfonate, are extremely hygroscopic and/or sensitive to the moisture, therefore they must be storage and processed under strictly controlled environmental conditions, with all the consequent economical and technological disadvantageous implications.

At present, the hygroscopic salts of SAMe are preserved and marketed in bulk as an anhydrous powder, prepared for example by lyophilization or spray-drying under strictly controlled temperatures, as described in EP141914, or in the pharmaceutical form of coated tablets. On the contrary other pharmaceutical forms, such as for example capsules, more handy and cheaper, are not practicable because rapidly damaged by the dehydrating action of the salt itself.

The instability of SAMe is accelerated, besides the heating, by an acidic medium too, hence the product, after administration, undergoes a significant decomposition at gastric level with a consequent variable intestinal absorption and an uncertain therapeutical dosage. In this case, therefore, it becomes fundamental to protect the tablets with a gastro-resistant coating, further increasing the production costs and terms.

As far as we know, because of all the above discussed problems, SAMe has never been formulated as a granulate.

We have now surprisingly found that the water-soluble salts of SAMe can be granulated providing stable, non hygroscopic and, optionally, gastro-resistant granulates with a simple, cheap and industrially applicable process.

Those granulates are a very advantageous form for the storage and the administration of the hygroscopic salts of SAMe and can be conveniently used by direct compression, optionally with the addition of suitable excipients, for manufacturing simple or coated non hygroscopic tablets or directly used for filling capsules.

Another advantage of the granulates in object consists of the possibility to formulate the SAMe together with other active drugs, in order to produce stable and non hygroscopic pharmaceutical forms.

Finally, if the gastro-resistant granulate is directly used during the preparation of tablets and capsules, it is possible to avoid the coating step or the use of special capsules, with significant saving of costs and time.

SUMMARY OF THE INVENTION

It is, therefore, an object of the present invention a process for the manufacture of granulates comprising a water-soluble salt of S-adenosylmethionine which comprises:

a) the simultaneous, sequential or alternate dispersion of at least a solution of a water-soluble salt of SAMe (A) and of a solution of a coating agent (B), on a fluid bed granulation carrier (C) and b) the fluid bed granulation of the mixture.

A second aspect of the invention is represented by the granulates, optionally gastro-resistant, obtainable by the above process.

A further object consists of solid oral pharmaceutical forms obtainable starting from the above granulates and comprising said water-soluble salt of SAMe, alone or optionally associated with other active drugs.

Finally, the last aspect of the present invention consists of using said granulates for manufacturing oral compositions, for therapeutical or feeding applications.

DESCRIPTION OF THE INVENTION

The granulation process object of the present invention is performed in classical fluid bed dryers, in which the solutions, containing the active drugs and the excipients, are sprayed onto the inert carrier and dried by a hot air flow.

Generally, in these devices, the rate of preparation of the granulate depends on the flow, moisture and temperature of the air introduced into the system, besides the speed of the addition of the solutions.

While it is possible to vary quite freely both the amount of the solvent and the flow and moisture of the air, it is instead preferable to take particular care of the applied temperature.

In fact, due to the significant thermolability of the active drug, it is advisable not to heat the product above 62° C., more preferably not above 52° C. Generally it is preferable to operate at a temperature between 48 and 52° C. and to complete the granulation by cooling the mass, preferably with air or nitrogen.

With the aim to further reduce the risk of degradation of the active product, it is possible to perform all the granulation procedure under an inert atmosphere, for example under nitrogen atmosphere.

Usable water-soluble salts of SAMe are the water-soluble salts stable enough under the process conditions. Sulfates, tosylates and 1,4-butandisulfonates are preferred among the water-soluble, simple or mixed, salts in which the anions are particularly bulky. The disulfate tosylate of SAMe is especially preferred due to its solubility. Hereinafter, for the sake of conciseness, the water-soluble salts of SAMe will be named as "salts of SAMe".

The salt of SAMe, according to the present invention, is dissolved in the selected solvent and, subsequently, dispersed onto the carrier.

Generally, being products for therapeutical or feeding use, it is preferable to employ water as a favorite solvent. Nevertheless it is possible to substitute the aqueous solvent, partially or completely, with other compatible solvents, provided that a good dissolution of the active drug is achieved.

On this purpose, the addition of solubilizing agents or surfactants can be considered.

The concentration of the solution of the salt of SAMe, preferably of its aqueous solution, can vary according to several parameters. On the one end the use of solutions too diluted is not advisable because it increases the drying time and, consequently, the risk of product degradation, on the other end it is necessary to stay under the solubility limit of the product at the spraying temperature, in order to avoid the precipitation of solids that could obstruct the nozzles of the devices. The solubility of the active drug depends on the salt, the solvent, the temperature and the presence of other components optionally dissolved. In particular, in the case of aqueous solutions, concentrations of the salt of SAMe, preferably of the disulfate tosylate, between 10 and 25% by weight, more preferably between 15 and 20%, are used.

With the aim to avoid the degradation of the compound, those aqueous solutions are prepared at the time of use or prepared and kept at a temperature ranging from −15° C. to +4° C. and brought to the use temperature, usually at about +15° C., just before use.

The granulation process of the present invention provides for the simultaneous, sequential or alternate dispersion of the above solution of the salt of SAMe (A) and of a solution of a coating agent (B).

Suitable coating agents according to the present invention, are organic polymers able to swell and form an adhesive film such as, for example, chitins, carragenins, cellulose and chemically modified celluloses, gum, xanthane and others. Hydroxypropylmethylcelluloses, in particular the hydroxypropylcelluloses that, in a 2% by weight aqueous solution, show a viscosity comprised from 4000 to 15000 cPs, such as, for example, those marketed with the name of Pharmacoat and Methocel, are preferred coating agents.

The concentration of coating agent in solution, preferably in the aqueous solution, is generally comprised from 5 to 15% by weight, preferably from 7 to 10%.

The granulation process, object of the present invention, provides for the dispersion of the salt of SAMe (A) and the coating agent (B), onto a carrier for fluid bed granulation (C).

With the term "carrier for fluid bed granulation", a pharmaceutically acceptable inert carrier, having the right granulometry, generally from 50 to 500μ, preferably from 100 to 200μ, for use in fluid bed dryers, that allows the preparation of granulates suitable for storage and marketing of the active drug, for the direct administration thereof or for a subsequent formulation in form of capsules or tablets, is meant.

In particular, the final granulate, according to its use, shall have the right flowability and bulk density for filling capsules or the ideal mechanical requirements for being compressed.

Starch, cellulose and maltodextrin can be named, as an example, among the carriers usable for preparing the granulates in object. In the present process microcrystalline cellulose is particularly advantageous, especially the cellulose marketed with the name of Vivapur 12 ® or PH101.

Carriers for granulation, according to the present invention, can optionally contain water in a variable amount. As an example, in case of marketed microcrystalline cellulose, the percentage of water is about 4%.

Preferably, in the granulation process according to the present invention, the amounts of the water-soluble salt of SAMe (A), of the coating agent (B) and of the carrier (C) are such as to provide a final granulate that comprises up to 60% of the water-soluble salt of SAMe (A), from 5 to 15% of the coating agent (B) and from 25 to 45% of the carrier (C) by weight with respect to the weight of the granulate itself, and even more preferably, from 48 to 55% by weight of (A).

Besides the above mentioned components, that is the salt of SAMe (A), the coating agent (B) and the fluid bed granulation carrier (C), the process in object may provide for the addition of other pharmaceutical excipients. In fact, depending on the subsequent use of the granulate, the additional more suitable excipients and the ideal operating conditions will be selected. Nevertheless, it is important to underline that those excipients are not directly responsible for the stability and non-hygroscopicity of the granules, but only allow improving some particular technological properties of the product.

As an example, when the granulate prepared according to the present process is employed for compression, it can be advantageous to add a surfactant, in order to reduce the disintegration time of the final tablets. Preferably the dispersion of the surfactant onto the granulate is performed at the end of the present granulation procedure. Surfactants suitable for that use are, as an example, the non-ionic surfactants derived from sorbitane or other surfactants commonly used in pharmaceutical technology, among them lauryl sulfate and polysorbate 80 are particularly suitable for the present granulation process.

With the aim to make the granulate gastro-resistant suitable coating agents may be applied, preferably at the end of the present granulation process. In that case the gastro-resistant granulate will be advantageously compressed or used for filling capsules, thus directly providing pharmaceutical forms suitable for the oral administration of SAMe.

Suitable gastro-resistant coating substances are, for example, acrylic polymers and lakes of Shellac type (Merck Index 13$^{th}$ Ed. page 8557). In particular, copolymers of methacrylic acid with ethyl acrylate, commonly marketed with the name of Eudragit ®, especially Eudragit®, are preferably used.

A further example of additional pharmaceutical excipients usable for the present invention is represented by lubricants, such as magnesium stearate, stearic acid, oils, hydrogenated fats, and by flowing agents such as talcum and silica, commonly used to improve the rheological properties of powders and granulates in the preparation of solid formulations.

Silica, in particular the colloidal silica marketed as Aerosil 200®, is particularly advantageous for the preparation, according to the present invention, of granulates employed for compression or filling of capsules.

In the granulation process of the present invention, depending on the subsequent use of the granulate and the pharmaceutical form obtained therefrom, besides the excipients above mentioned, other commonly used excipients, such as, for example, sweeteners, e.g. saccharin, aspartame, cyclamate or similar, dyes, sparkling components, for example mixtures of tartaric acid and sodium bicarbonate, or flavoring agents, may optionally be used.

According to the granulation process of the present invention the dispersion of the solutions containing, respectively, the salt of SAMe (A) and the coating agent (B) and, optionally other additional excipients, may be simultaneous, sequential or alternate.

The conditions of the addition of the components and the duration of the spraying steps may vary depending on the kind of granulate wanted and its subsequent use. As an example, the simultaneous spraying of the solution of SAMe (A) and of the coating agent (B) generally gives the granulate a capillary protection, that makes it more resistant to the exposure to the air and, therefore, particularly suitable for filling capsules.

In such a case, the two components and the optional excipients, will be dissolved in separated solutions or, if chemically compatible, in the same aqueous solution. In the case of a sequential dispersion, the solution of the coating agent is sprayed only after the addition of the solution of SAMe onto the carrier is finished. The resultant granulate, characterized by a superficial coating, quicker to be placed and cheaper, has very good breaking up capabilities that allow its direct use in preparing tablets.

Instead the alternate addition of the solution of SAMe (A) and of the coating agent (B) allows the preparation of a granulate having a stratified structure.

In such a case, by appropriately selecting the most suitable additional excipients, it is possible to prepare a slow or programmed release granulate usable, directly or after an additional formulation, for a less frequent oral administration of the active drug.

Regarding the conditions of addition of the other excipients optionally used, it is preferable for example to disperse the gastro-resistant agent and the surfactant at the end of the spraying of the salt of SAMe, while the lubricant agent can be indifferently added at every step of the process, even at the beginning, that is directly onto the granulation carrier.

In conclusion, the level of protection of the granulate prepared according to the present method depends on a set of elements such as the conditions of the addition of the components, the amount of the coating agent used and the presence of other excipients. The optimization of the preparation method of the granulate in object, depending on its destination, may be achieved by an appropriate modification of the process parameters up to now considered and, anyway, it is comprised among the common functions and capabilities of the man skilled in the art.

Another aspect of the invention is represented by the granulates obtainable with the present process and by the pharmaceutical forms obtainable by the granulates themselves.

Those granulates may contain high amounts of the salt of SAMe and generally comprise up to 60% of the water-soluble salt of SAMe (A), from 5 to 15% of the coating agent (B) and from 25 to 45% of the carrier (C) with respect to the weight of the granulate itself, even more preferably from 48 to 55% by weight of (A).

In addition, they may show a content of residual water generally comprised from 2 to 3% by weight, that usually is not detrimental to the stability of the salt of SAMe contained.

The granulate, prepared according to the process in object, is characterized by a bulk density usually comprised between 330 and 450 g/l, appropriately modifiable depending on the destination of the granulate itself.

That granulate may be simply assigned to the storage and marketing of the active drug or may be advantageously used for the preparation of different pharmaceutical forms. For example, depending on the additional excipients selected, the granulate may be useful for the preparation of extemporary oral suspensions, optionally effervescent, of solid oral forms, such as effervescent, chewable or controlled-release tablets, including gastro-resistant tablets, or capsules. Generally, the optimization of those formulations is among the normal capabilities and knowledge of the skilled in the field.

A further aspect of the present invention is represented by pharmaceutical compositions comprising a granulate of a hygroscopic salt of SAMe, prepared with the granulation method in object, in combination with one or more different active drugs.

In the literature, several examples of an associated use of SAMe with other active drugs are described, for example in the prevention and treatment of the inflammation of the connective tissue (WO99/62524 e WO98/48816), of hepatic pain (WO99/43336) and in the inhibition of HIV replication (EP827964 and DE19628514).

However, as far as we know, pharmaceutical compositions of SAMe associated with other active drugs or nutriments do not exist on the market, probably because of the low stability of the hygroscopic salts of SAMe.

On the contrary those compositions can be advantageously realized by using the stable and non hygroscopic granulate of SAMe of the present invention.

On that purpose the salt of SAMe and every other active drug selected for the association, can be granulated together according to the present process, starting from a single solution or from separated solutions. Alternatively, in case of chemical incompatibility among the active drugs, it will be possible to formulate in advance the salt of Same according to the present invention and subsequently combined the so obtained granulate with the other active drugs under the most suitable form. As an example different granulates will be mixed and the resultant mixture will be used for extemporary oral preparations, for manufacturing tablets or for filling capsules.

According to a preferred embodiment of the granulation process of the present invention, the aqueous solutions of SAMe disulfate tosylate (A), of Pharmacoat 615 and, optionally, of Aerosil 200, are sprayed, simultaneously or successively, onto the microcrystalline cellulose carrier in a fluid bed granulator and granulated, at a temperature not higher than 52° C. and for the time needed for obtaining the desired granulate. Optionally, at the end of this preliminary phase, the aqueous solutions containing Eudragit L or lauryl sulfate will be dispersed onto the granulate and then the granulation is continued, at the ideal temperature and time. Finally, once the granulation step is finished, the air-cooling of the granulate is performed.

These and other aspects of the invention will be better illustrated by the following examples and that, nevertheless, have not to be considered limiting of the invention itself.

EXAMPLES

Preparation of the Granulate

In the examples disclosed hereinafter the following materials and devices, which can be substituted by equivalent materials or devices, were used:

Fluid bed dryers:
Hüttlin HKC-50-TJ
Glatt WST 30, vertically structured, with top spray, equipped with peristaltic pump. Bed volume: 94 l.
Water-soluble salts of SAMe:
S-adenosylmethionine disulfate tosylate (m.w. 766,8, Pliva)
Coating agents:
hydroxypropylmethylcellulose (Pharmacoat 615, Methocel E4M, Methocel K15M Premium type)
Carriers for granulation:
Microcrystalline cellulose (Avicel PH101, Vivapur 12® type)
Maltodextrin (Cerestar)
Other excipients:
lubricants: colloidal silica (Aerosil 200 type)
surfactants: sodium lauryl sulfate, polisorbate 80
gastro-resistant coatings: acrylic and methacrylic polymers (Eudragit L type)

Example 1

Preparation of a Granulate of SAMe, with the Addition of a Lubricant, (Simultaneous Spraying)

The 10% by weight aqueous solution of SAMe disulfate tosylate (250 Kg, corresponding to 25 Kg of salt of SAMe), kept at +4° C. and warmed up to 15° C. before using, was transferred into a 300 liters stainless steel container, equipped with a propeller mixer. Hydroxypropylmethylcellulose (HPMC, Pharmacoat 615) (5 Kg) and after mild stirring for 25', silica (Aerosil 200) were added to the solution and the stirring was continued for other 15' up to the complete dissolution of the components.

The solution was then sprayed for 13 hours onto Vivapur ® 12 microcrystalline cellulose (15 Kg), in a fluid bed granulator Hüttlin HKC-50-TJ, in which the highest temperature of the outlet air was 49° C. At the end of the granulation the temperature of the product was 48° C. The granulate was then dried for 10' more and cooled for 25', with a temperature of the outlet air of 42° C.

The final granulate showed the following per cent composition:

| Ingredients | % (by weight) |
| --- | --- |
| SAMe Disulfate Tosylate | 54.3 |
| Pharmacoat 615 | 10.9 |
| Aerosil 200 | 2.2 |
| Vivapur ® 12 | 32.6 |
| Total | 100 | with a content of water equal to 2.42% w/w (loss on drying IR 105° C. for 15') and a density of 420 g/l.

The yield of the granulation process was 95.43% (theoretical: 46.00 Kg, experimental 43.90 Kg).

Example 2

Preparation of a Granulate of SAMe (Sequential Spaying)

The 20.7% by weight aqueous solution of SAMe disulfate tosylate (75.7 Kg, equal to 15.68 Kg of salt of SAMe), kept at −15° C. warmed up to 15° C. before using, was sprayed onto microcrystalline cellulose (14.852 Kg, PH101, humidity 4.25%) in a Glatt WST 30 fluid bed granulator, and granulated for 8 hours and 40 min. at a maximum temperature of the outlet air equal to 52° C. The final temperature of the product was 44° C. The granulated was coated with Pharmacoat 615 (0.632 Kg in a 7% by weight aqueous solution) in the same device, for 1 hour and 10 min. and then cooled with air for 20' (air outlet T after cooling 46° C.). The final granulate showed the following per cent composition:

| Ingredients | % (by weight) |
| --- | --- |
| SAMe Disulfate Tosylate | 50.3 |
| Pharmacoat 615 | 2.0 |
| PH101 | 47.7 |
| Total | 100 | with a content of water equal to 2.61% w/w (loss on drying IR 105° C. for 15') and a density equal to 330 g/l.

The yield of the granulation process was 96.4% (theoretical: 31.16 Kg, experimental 30.04 Kg).

Example 3

Preparation of a Granulate of SAMe, with Addition of Lubricants (Sequential Spraying)

In this example, that is a variant of example 2, Aerosil 200 (0.9 Kg) was directly mixed with the carrier PH101 (13.5 Kg) before granulating. The mixture was then charged into the granulator and the fluid bed granulation was performed, with the sequential addition of the salt of SAMe (15 Kg of SAMe disulfate tosylate) and of the coating agent (0.6 Kg of Pharmacoat 615) under the same operating conditions described in example 2.

The final granulate showed the following per cent composition:

| Ingredients | % (by weight) |
| --- | --- |
| SAMe Disulfate tosylate | 50.0 |
| Pharmacoat 615 | 2.0 |
| Aerosol 200 | 3.0 |
| PH101 | 45.0 |
| Total | 100 |

The presence of 3% of Aerosil 200 increased the flowability of the final granulate, improving the performance in tablet preparation.

Example 4

Preparation of a Granulate of SAMe for Filling Capsules.

In this example maltodextrin (12 Kg) instead of microcrystalline cellulose was used as a carrier, and then we went on according to the operating conditions quoted in the example 2, starting from 15 kg of SAMe disulfate tosylate and 0.9 Kg of Pharmacoat 615.

The final granulate showed the following per cent composition:

| Ingredients | % (by weight) |
|---|---|
| SAMe Disulfate Tosylate | 53.8 |
| Pharmacoat 615 | 3.2 |
| Maltodextrin | 43.0 |
| Total | 100 |

The presence of maltodextrin improved the performance of the granulate in the preparation of capsules. The granulate, in fact, showed a bulk density of 370 g/l and could contain a greater amount of the active drug.

Example 5

Preparation of a Granulate for Compression

A batch of the final granulate, prepared according to the conditions described in example 1, by granulating an aqueous solution of SAMe disulfate tosylate (20 Kg of a 10% by weight aqueous solution), of Pharmacoat 615 (4 Kg), Aerosil 200 (0.8 Kg) and of Vivapur®12 (12 Kg) was sprayed with an aqueous solution of lauryl sulfate (0.6 Kg dissolved in 5 l of water) for 20', under the same operating conditions used for example 1.

The final granulate showed the following per cent composition:

| Ingredients | % (by weight) |
|---|---|
| SAMe disulfate tosylate | 53.5 |
| Pharmacoat 615 | 10.7 |
| Aerosil 200 | 2.1 |
| Vivapur ® 12 | 32.1 |
| Lauryl sulfate | 1.6 |
| Total | 100 |

The so obtained granulate was particularly suitable for the manufacture of tablets. The procedure herein described, could be repeated, in a similar manner, starting from the final granulates prepared in the examples 2, 3 and 4.

Example 6

Preparation of a Gastro-Resistant Granulate

A batch of a final granulate, prepared according to the examples 1, 2 or 4, was coated with a gastro-resistant coating.

At the end of the granulation, an aqueous solution of Eudragit L was dispersed onto the granulate and evaporated under conditions similar to those already reported. The percentage of Eudragit, calculated on the final granulate, varied from 1.5 to 2.5% by weight.

The so obtained granulate was particularly suitable for filling capsules.

Stability Test on the Granulate

Example 7 (Comparison Example)

The test was performed by comparing the granulates prepared according to the examples 1, 2, 3, 4, 5 and 6 with a reference mixture of powders (standard), the composition thereof corresponds to the medicinal product containing SAMe presently on the market (tablets SAMYR® by Knoll Pharmaceuticals containing 200 mg of SAMe disulfate tosylate).

The per cent composition of the reference mixture is the following:

| Ingredients | % (by weight) |
|---|---|
| SAMe disulfate tosylate | 53.2 |
| D-mannitol | 39.6 |
| Aerosil 200 | 2.7 |
| Magnesium Stearate | 1.8 |
| Sodium Bicarbonate | 2.7 |
| Total | 100 |

Samples of granulates, from the experiments 1, 2, 3, 4, 5 e 6 and from the reference mixture, were prepared by introducing 10 g. of the product in a polyethylene double bag and by sealing the bag itself, under normal atmosphere. For each product 12 samples were prepared and kept at a mean temperature of 25° C. and at a relative percentage of humidity equal to 60%. The visual and instrumental (Karl-Fischer and HPLC) analysis of the samples was performed every 2 weeks for a total time of 24 weeks, with the following results:

SAMe Granulates

| Mean analytical parameters | Week 0 | Week 12 | Week 24 |
|---|---|---|---|
| Appearance | Cream colored granules | In compliance | In compliance |
| Content of water (K.F.) (%) | 2.5–3.5 | 3.0–3.5 | 3.5–4.5 |
| Content of impurities HPLC (methylthioadenosine %) | 0.5–0.9 | 1.3–1.5 | 1.5–1.2 |

Reference Mixture

| Mean analytical parameters | Week 0 | Week 12 | Week 24 |
|---|---|---|---|
| Appearance | White powder | | |
| Content of water (K.F.) (%) | 1.0–1.5 | | |
| Content of impurities HPLC (methylthioadenosine %) | 0.5–1.0 | | |

After 3–4 weeks only, in some cases even less, the samples of the reference mixture were no more comparable. In fact the powder became a crumbly and sticky solid mass, characterized by the typical unpleasant smell of methylthioadenosine.

From the experiment it is evident that the granulates prepared according to the present process have characteristics of stability and non-hygroscopicity clearly higher than the compositions of SAMe corresponding to those available on the market.

Preparation of Tablets and Capsules

Example 8

Preparation of Tablets

A sample for each granulate, prepared according to the examples 1, 2, 3 and 5, was added with small amounts of D-mannitol and lubricating agents and used for evaluating the performances of the mixture to direct compressing. The composition of the resultant mixture was the following:

| Ingredients | amount (g) |
|---|---|
| SAMe granulate | 240 |
| D-mannitol | 15 |
| Magnesium stearate | 4.5 |
| Talc | 3.0 |

The mixtures were prepared and compressed under normal atmosphere, at a temperature of 22–26° C. and with a relative humidity of 50–75%.

A Ronchi alternative machine with convex round punches (12.5 mm) was used for the compression test by applying a pressure of 3–4 ton. The tablets showed the following parameters:

| Parameter | Measured value |
|---|---|
| Mean weight | 0.883 g (theoretical 0.875 g, S.D. 0.01619) |
| Height | 7.0–7.3 mm |
| Hardness (Schleuninger2E) | 39–60 newtons |
| Disgregation time | pH 1 > 1 h |
| | pH 6.8 < 1 h |

The tablets did not have a gastro-resistant coating but, due to the special protection of the granulate, their performances corresponded to those of coated tablets.

Example 9

Preparation of Tablets (Comparative Example)

A compression test under the same environmental conditions and with the same machine of example 8 was performed, using as a mixture the reference mixture of powders described in the example 7.

After few minutes the reference product was too sticky to be handled and the compressing machine was stopped in order to avoid damages to the mechanical parts. In conclusion, the reference mixture, corresponding to the compositions of SAMe currently on the market, is too hygroscopic to be handled under standard atmosphere.

Example 10

Preparation of Capsules

A sample for each granulate prepared according to the example 4 and 6, was added with small amounts of lactose and lubricant agents and used for evaluating the performances of the mixtures in filling capsules of the Snap-fit kind.

The composition of the resultant mixtures was the following:

| Ingredients (mg) | 00 Dimension | 0 Dimension | 1 Dimension |
|---|---|---|---|
| SAMe granulate | 400 | 25 | 150 |
| lactose | 50 | 30 | 50 |
| Magnesium stearate | 10 | 10 | 5 |
| Talc | 5 | 5 | 2 |
| Total | 465 | 295 | 207 |
| Mean gross weight | 585.3 | 390.2 | 288.5 |

The mixtures were prepared and used under standard atmosphere, at a temperature of 22–26° C. and with a relative humidity of 50–75%.

A compact kind MG2 encapsulating machine was used for the preparation of capsules. The capsules so obtained, due to the properties of the granulates prepared according to the present method, were more stable than those prepared by using salts of SAMe non-granulated according to the process of the present invention.

Preparation of Associated Compositions.

The granulate of SAMe, due to its characteristics of stability, can be formulated together with other active drugs or nutriceuticals, for the preparation of therapeutical, dietetic and/or integrator products, as illustrated in the following examples:

Example 11

| Integrator products for the elders 500 mg Tablets | |
|---|---|
| SAMe Granulate (titre 50%) | mg. 200.0 |
| Vitamin E (50%) | mg. 10.0 |
| Ginko biloba dried exctr. | mg. 20.0 |
| Lactose | mg. 200.0 |
| Microcrystalline cellulose | mg. 50.0 |
| Talc | mg. 10.0 |
| Magnesium stearate | mg. 10.0 |

Example 12

| Integrator product for enhancing the hepatic performance 500 mg Tablets | |
|---|---|
| SAMe Granulate (titre 50%) | mg. 200.0 |
| Vitamin B1 | mg. 0.7 |
| Thistle dried exctr. | mg. 50.0 |
| Lactose | mg. 200.0 |
| Microcrystalline cellulose | mg. 50.0 |
| Talc | mg. 10.0 |
| Magnesium stearate | mg. 10.0 |

The invention claimed is:

1. A process for manufacturing granulates containing a water-soluble salt of S-adenosylmethionine (SAMe) comprising:
   a) simultaneously, sequentially or alternately dispersing at least a solution of a water-soluble salt of SAMe and a solution of a coating agent onto a carrier disposed in fluid bed granulation to obtain a mixture; and b) granulating said mixture at a temperature not above 62° C. to obtain a granulate; wherein said solutions are aqueous solutions.

2. A process according to claim 1 wherein said fluid bed granulation is performed at a temperature from 48° C. and 52° C..

3. A process according to claim 1 wherein the water-soluble salt of SAMe is a salt of SAMe is selected from the group consisting of sulfate, tosylate and 1,4-butandisulfonate.

4. A process according to claim 3 wherein said salt is SAMe disulfate tosylate.

5. A process according to claim 1 wherein the solution of the water-soluble salt of SAMe has a concentration from 10 to 25% by weight.

6. A process according to claim 1 wherein the coating agent is selected from the group consisting of chitins, carragenins, cellulose, chemically modified celluloses, gum and xanthane.

7. A process according to claim 6 wherein the coating agent is a hydroxypropylmethylcellulose.

8. A process according to claim 1 wherein the solution of the coating agent has a concentration from 5 to 15% by weight.

9. A process according to claim 1 wherein the fluid bed granulation carrier is selected from the group consisting of starch, cellulose and maltodextrin.

10. A process according to claim 1 wherein the fluid bed granulation carrier is characterized by a granulometry from 50μ to 500μ.

11. A process according to claim 1 characterized by comprising an additional coating step with a gastro-resistant coating agent.

12. A process according to claim 5 wherein the solution of the water-soluble salt of SAMe has a concentration from 15 to 20% by weight.

13. A process according to claim 8 wherein the solution of the coating agent has a concentration from 7 to 10% by weight.

14. A process according to claim 9 wherein the fluid bed granulation carrier is microcrystalline cellulose.

15. A process according to claim 10 wherein the fluid bed granulation carrier is characterized by a granulometry from 100μ to 200μ.

16. A process according to claim 1 wherein the coating agent is hydroxypropylmethylcellulose and the carrier is microcrystalline cellulose.

17. A process according to claim 1 wherein the coating agent is selected from the group consisting of cellulose and chemically modified cellulose, and the carrier has a granulometry from 50μ to 500μ.

18. A process according to claim 1 wherein the coating agent is hydroxypropylmethylcellulose and the carrier has a granulometry from 50μ to 500μ.

19. A process according to claim 18, wherein the coating agent is hydroxypropylmethylcellulose and the carrier has a granulometry from 100μ to 200μ.

20. A process according to claim 1 wherein the coating agent is hydroxypropylmethylcellulose and the carrier is microcrystalline cellulose having a granulometry from 100μ to 200μ.

21. A process for manufacturing granulates containing a water-soluble salt of S-adenosylmethionine (SAMe) comprising:

a) simultaneously, sequentially or alternately dispersing an aqueous solution comprising up to 60% by weight of a water-soluble salt of SAMe and an aqueous solution of 5–15% by weight of a coating agent onto 25–45% by weight of carrier disposed in a fluid bed granulation to obtain a mixture; and b) granulating said mixture at a temperature not above 62° C. to obtain a granulate.

22. A process according to claim 21, wherein said aqueous solution is prepared at the time of use at a temperature between −15° C. and −4°.

23. A process according to claim 1, wherein said aqueous solution is prepared at the time of use at a temperature between −15° C. and +40°.

* * * * *

UNITED STATES PATENT AND TRADEMARK OFFICE
CERTIFICATE OF CORRECTION

PATENT NO.        : 7,048,948 B2                                    Page 1 of 1
APPLICATION NO. : 10/432338
DATED             : May 23, 2007
INVENTOR(S)       : Cantabene Carlo It is certified that error appears in the above-identified patent and that said Letters Patent is hereby corrected as shown below:

Title Page—(73) Assignee attorney for the Assignee respectfully requests a Certificate of Correction to reflect the partial Assignee of record, namely:

Chemistry and Health International BV, Lugano, Switzerland

Signed and Sealed this

Fourteenth Day of April, 2009

JOHN DOLL
*Acting Director of the United States Patent and Trademark Office*

UNITED STATES PATENT AND TRADEMARK OFFICE
CERTIFICATE OF CORRECTION

PATENT NO.        : 7,048,948 B2                                Page 1 of 1
APPLICATION NO.   : 10/432338
DATED             : May 23, 2006
INVENTOR(S)       : Cantabene Carlo It is certified that error appears in the above-identified patent and that said Letters Patent is hereby corrected as shown below:

Title Page—(73) Assignee attorney for the Assignee respectfully requests a Certificate of Correction to reflect the partial Assignee of record, namely:

Chemistry and Health International BV, Lugano, Switzerland

This certificate supersedes the Certificate of Correction issued April 14, 2009.

Signed and Sealed this

Fifth Day of May, 2009

JOHN DOLL
*Acting Director of the United States Patent and Trademark Office*